United States Patent [19]
Schulman

[11] Patent Number: 5,355,896
[45] Date of Patent: Oct. 18, 1994

[54] VAGINAL PESSARY

[76] Inventor: Norman Schulman, 250 N. Robertson Blvd., Beverly Hills, Calif. 90211

[21] Appl. No.: 21,193

[22] Filed: Feb. 23, 1993

[51] Int. Cl.⁵ .............................................. A61F 6/06
[52] U.S. Cl. ..................... 128/834; 128/835
[58] Field of Search ............... 128/830–841, 128/842

[56]  References Cited

U.S. PATENT DOCUMENTS

| | | | |
|---|---|---|---|
| 60,312 | 12/1806 | Willens | 128/834 |
| 163,871 | 1/1875 | Kean | 128/834 |
| 183,832 | 10/1876 | Barnett | 128/834 |
| 436,861 | 9/1890 | Sherwood | 128/835 |
| 726,532 | 4/1908 | Hering | 128/835 |
| 2,452,229 | 10/1948 | Bray | 128/834 |
| 2,540,325 | 6/1951 | Bray | 128/834 |

FOREIGN PATENT DOCUMENTS 0055186  9/1912  Fed. Rep. of Germany ...... 128/838

OTHER PUBLICATIONS

"19 Common Uses of the Milex Supportive Pessary", Brochure.

*Primary Examiner*—Michael A. Brown
*Attorney, Agent, or Firm*—Spensley Horn Jubas & Lubitz

[57] ABSTRACT

A pessary having a substantially flat, circular, flexible head substantially rigid across its diameter, compressible through operation of an attached manipulation apparatus. The pessary may include a lock to hold the head in a desired shape and an irrigation channel to permit cleansing of the vagina and pessary.

10 Claims, 8 Drawing Sheets

VAGINAL PESSARY

BACKGROUND OF THE INVENTION

1. Field of the Invention

This invention relates to an artificial, non-surgical means of supporting the bladder, the rectum, the bowel, the vagina and/or the uterus of women who have poor vaginal wall support.

2. Description of Related Art

Vaginal support devices have been known to exist for many centuries. The need for such medical prostheses is by no means a recent occurrence. Various appliances have been used over the ages, although they all are meant to achieve the same end. Namely, these devices add to the support of the vaginal wall in order to help prevent prolapse of the uterus and/or bladder and/or the rectum through the vaginal opening.

At the present time, there are various appliances in use. However, there are certain objections that are shared by all of the presently available devices. Among these objections is the fact that a physician has to fit the proper size, as all pessaries are of a fixed size, and, therefore, must be fitted individually according to the patient's needs. Inherent in this rigidly structured system is that if the best size for a given patient were to fall between the sizes that were manufactured, then that patient would be deprived of her optimal size. In addition, most women have difficulty removing and/or replacing the pessary by themselves, and this necessitates repeated doctor visits to remove the pessary, clean or replace it with a new pessary, and then reinsert the pessary. Moreover, because of the constant and prolonged use of an indwelling pessary, a frequent complaint of users of these devices is that vaginal mucus and bacterial build-up creates infection, foul odor and significant secretions, all of which can be unpleasant, annoying and embarrassing. It should be pointed out that many patients requiring a vaginal pessary are elderly, and not infrequently have diminished mobility due to their age and concomitant impairments. indeed, one of the greatest scourges that frequently occurs in older age women is urinary incontinence, which can be a direct result of vaginal prolapse. Often, these women are left to decide between wearing absorptive diapers, or submitting to uncomfortable surgical procedures attended by all of the well-known risks associated with any surgical procedure. Even when the surgical route is selected there is no certainty that it will be successful, although the increasing costs associated with any surgical procedure, not to mention the additional hazards attached to surgery of the elderly, are certainly guaranteed. Moreover as there is an ever increasing number of older women, there is a growing population of patients with this problem.

Another significant obstacle has been that, to obtain an effective device, substantial sacrifices must be made. For example, highly effective devices are typically difficult to manipulate and, therefore, painful to remove and reinsert. This is so because the opening to the vagina is smaller in diameter than the vaginal cavity itself; and it is this difference which is utilized to keep various pessaries from failing out, or being expelled during instances of increased pelvic pressure. Hence, a pessary must be small enough to pass through the vaginal opening, but large enough so that it does not fall out. This requires a pessary that can either change its shape and/or size, or make use of another physical principle, such as surface tension.

SUMMARY OF THE INVENTION

It is, therefore, an object of the present invention to provide a single pessary that is flexible enough to change sizes, as well as have enough contact surface area to allow for the increased mechanism of surface tension to maintain the appliance in an intravaginal position such that it lends continual and effective support to the vaginal walls.

It is a further object of the present invention to provide a vaginal support prostheses that is malleable and adjustable such that a woman can easily, safely and comfortably insert and remove the device at will without medical assistance.

It is a further object of the present invention to provide a vaginal support device that has such a range of adjustment as to permit a single device to be able to span several different size ranges in order to permit an individual patient or her health professional to find her most optimal size, as well as make continual adjustments in its dimensions which would allow for progressive changes in size requirements.

It is yet a further object of the present invention to provide a vaginal support device that is not only easy to clean and maintain, but also which allows at the same time for a simple and accessible means by which the vaginal cavity can be kept free of unpleasant odor and discharge.

It is still another object of the present invention to provide a reliable and effective nonsurgical means of supporting the vaginal walls which reduces by a significant degree the amount of necessary intervention and maintenance by a health professional, and, therefore, helps to significantly reduce long term costs.

These objects and others are achieved by the provision of a vaginal pessary which can be comfortably worn and easily removed and replaced at will according to the needs of the wearer. Moreover, the present invention encourages use of such a pessary thereby obviating the need for more expensive and dangerous operative procedures by overcoming the major disadvantages of the vaginal appliances that have been used up to now.

The pessary of the present invention allows an individual to easily, comfortably and without medical risk or expense remove, clean and reinsert the device. The device also provides an easy mechanism to both clean and refresh the pessary as well as the vagina without the need to remove the device. In addition, the size may be adjusted within a range of sizes such that each individual device can be "custom fit" for the individual wearer, and further, that the size can be changed over time to allow for individual circumstances.

BRIEF DESCRIPTION OF THE DRAWINGS

These and other advantages of the present invention are best understood with reference to the drawings, in which.

Like numbers and designations in the drawings refer to like elements.

DETAILED DESCRIPTION OF THE PREFERRED EMBODIMENTS

The present invention is based essentially on a discovery that the vaginal walls can be comfortably and effectively supported through the use of a pessary having a range of adjustability. The comfort of the pessary to the user is further enhanced through its ease of insertion and removal and simple, fast and effective cleaning.

According to the present invention, the drawbacks described earlier herein can be eliminated, or at least substantially minimized, and the vaginal walls can be effectively and comfortably supported by the use of a pessary consisting of a flexible, circular head preferably connected to a syringe like base. The head is constructed so that it may be configured and adjusted through a narrow range of sizes while positioned in the vagina, and through manipulation of the base the head may be deformed temporarily for convenient insertion and removal.

Figure 1:
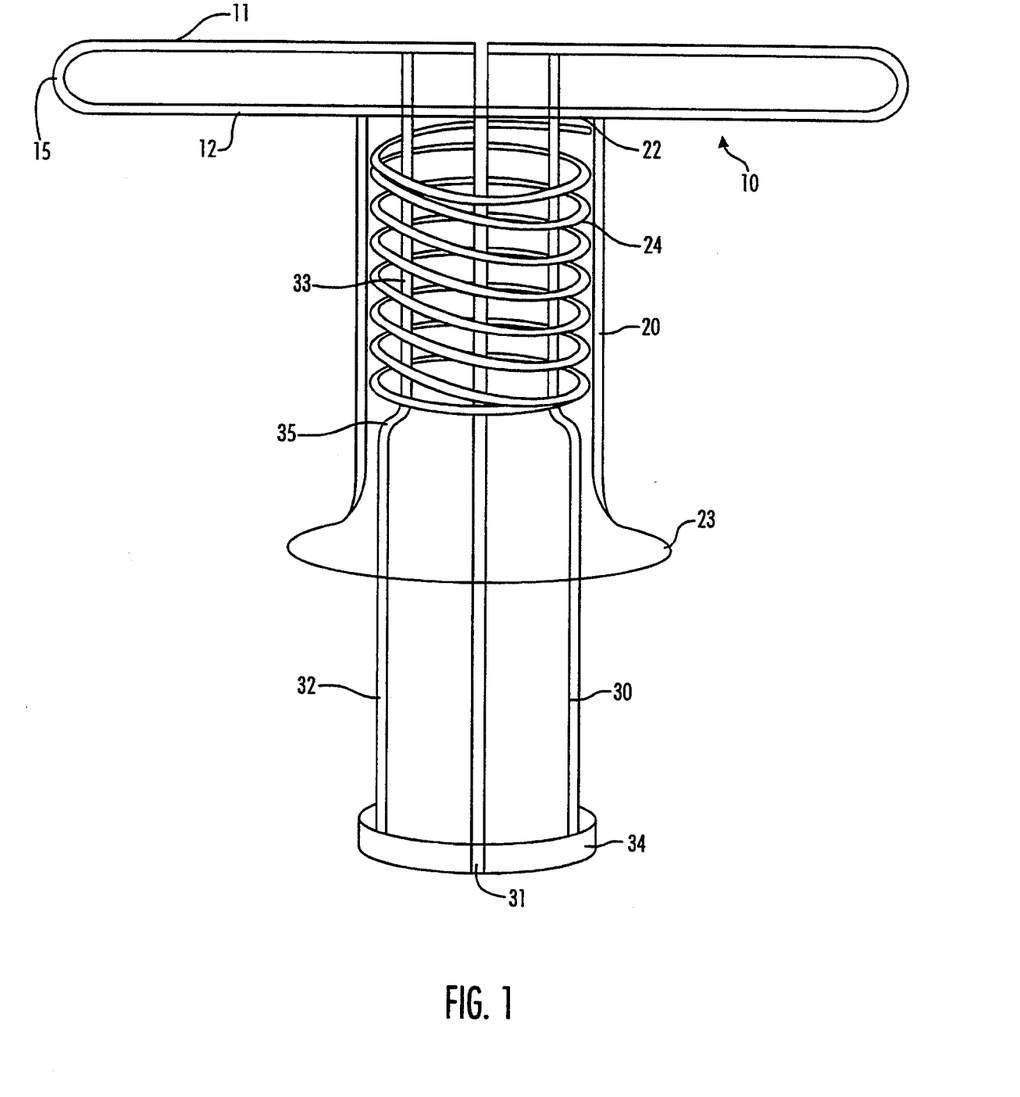
FIG. 1 shows a side sectional view of a pessary which embodies aspects of the invention in the fully extended position.

Referring now to FIG. 1 a first embodiment of the invention is described. This embodiment comprises three principal parts: a stretchable retaining head 10, a chamber 20 and a plunger 30. The chamber 20 and plunger 30 together comprise a manipulation apparatus for the head 10. Preferably, the manipulation apparatus is as small as possible to improve comfort. The various manipulation apparatuses shown in the drawings are not necessarily to scale.

Figure 2:
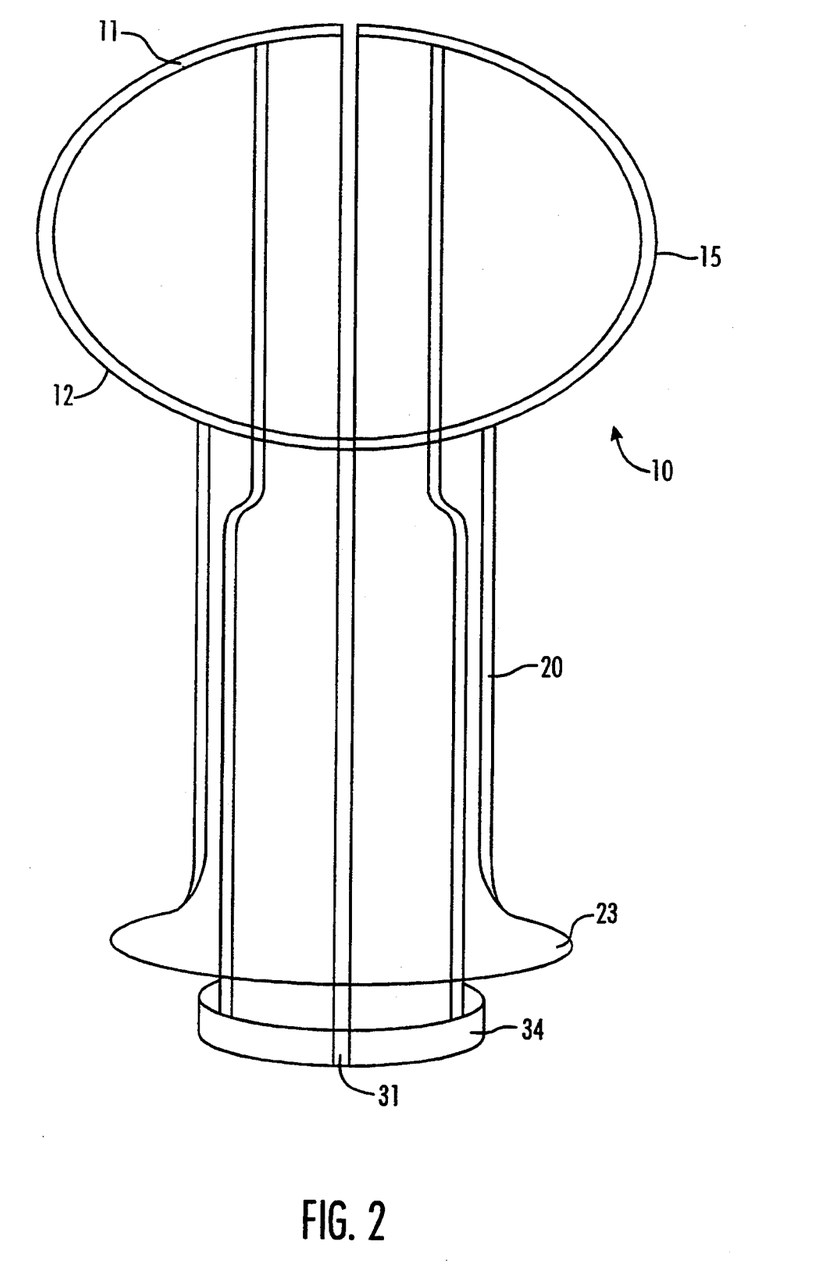
FIG. 2 shows a side sectional view of a pessary as in FIG. 1 in the compressed position.
Figure 9:
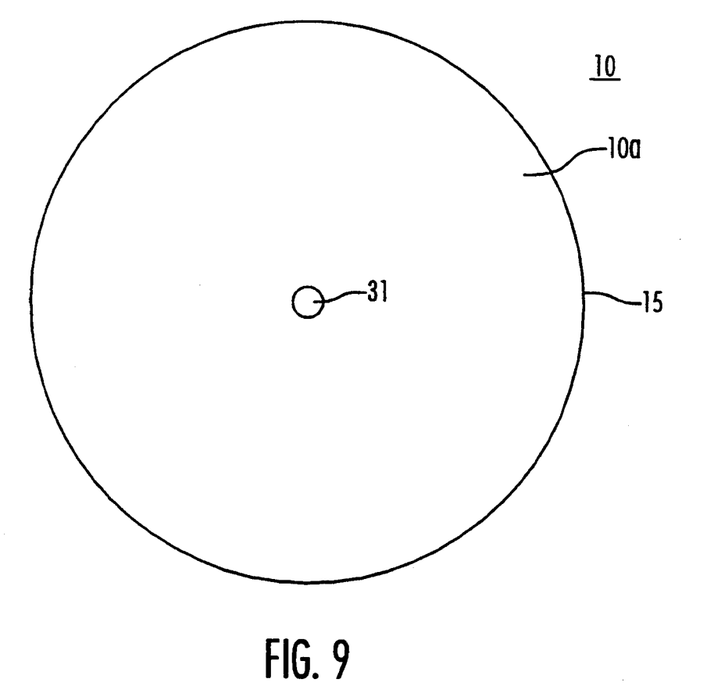
FIG. 9 shows a top view of a pessary of the present invention in the fully extended position.
Figure 10:
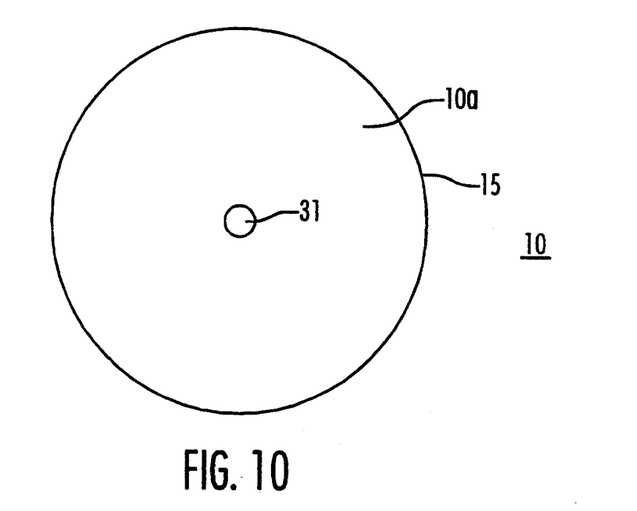
FIG. 10 shows a top view of a pessary of the present invention in the compressed position.

The pessary shown in FIG. 1 is in its fully expanded position. As can be seen in FIG. 9, the head 10 may be sized to the support needs of the patient. To insert the pessary, the head 10 is compressed to a sufficiently small diameter, as shown in FIG. 2. As shown in FIG. 10, the head 10 is also sized according to the insertion needs of the patient. Once inserted, the size of the head 10 may be controllably expanded to fit the vagina. Thus, the materials and dimensions of the head 10 provide both support and ease of insertion without compromise.

The head 10 is preferably substantially flat, circular, flexible and has structural integrity. The head 10 includes operative connectors to the chamber 20 and plunger 30. The embodiment as shown in FIG. 1 includes upper and lower operative connectors 11, 12 which allow for expandability of a rim 15, while maintaining some integrity of shape and function, The rim 15 is made preferably of plastic, latex or other inert material which is flexible but durable once inserted into the vagina. The rim 15 is connected to the chamber 20 and plunger 30 by operative connectors 11 and 12. The upper operative connector 11 is preferably connected to the plunger 30, and the lower operative connector 12 to the chamber 20. Thus, when the plunger 30 is pressed into the chamber 20 the upper operative connector 11 pulls the rim 15 upward, while the lower operative connector 12 holds the rim 15 downward, thus causing the rim 15 to deform and shrink in width. This permits easy insertion and removal of the pessary.

Figure 8:
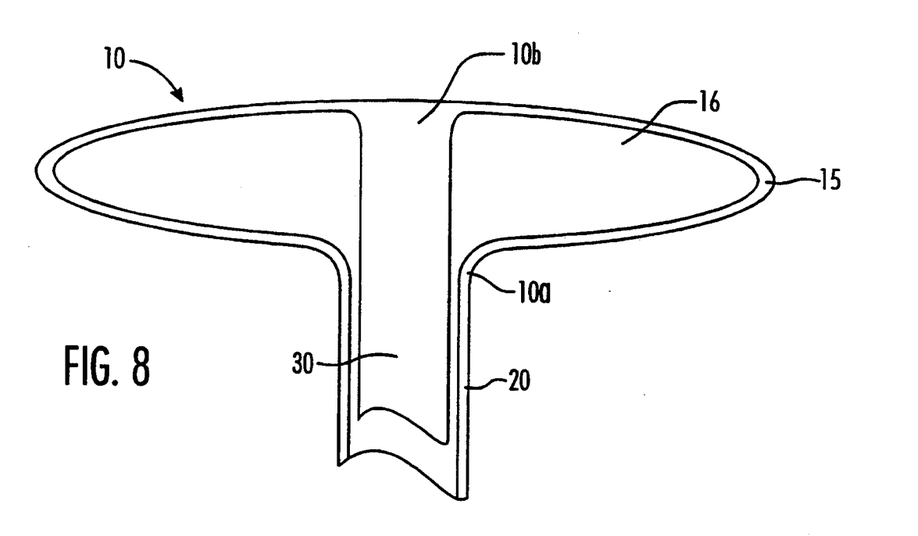
FIG. 8 shows a sectional view of a pessary of the present invention.

Referring now to FIG. 8 an alternative embodiment of the head 10 is described. The head 10 may comprise a pair of resilient disks 10a, 10b joined at their rims 15 and defining a cavity 16. An upper disk 10b comprising the upper side of the head 10 is attached to the plunger 30, and a lower disk 10a comprising a lower side of the head 10 to the chamber 20. In fact, so long as the head 10 is partially compressible from small compressive forces (to provide a good fit in the vagina) and highly compressible from large compressive forces (to permit installation and removal), the head 10 may be made of any of the materials known in the art. Furthermore, the head 10 may be manufactured as a unitary body having a cavity 16 obviating the need for separate upper and lower disks 10a, 10b that require sealing at their rims 15.

Referring again to FIG. 1, the person doing the insertion, be it the patient or health professional, grasps the chamber 20 much like a syringe, with two fingers at the chamber grip 23 and the thumb on the plunger end 34. Pressure on the plunger end 34 causes the plunger 30 to move relative to the chamber 20, and at the same time, push the upper operative connector 11 of the head 10 forward. This results in the altered size and shape of the device depicted as in FIG. 2. The pessary could then easily be inserted. Release of the plunger 30 allows the head 10 to return to the fully extended position as depicted in FIG. 1. Of course, it can be seen that there are numerous other techniques for grasping and manipulating the invention apparatus. The manner by which the pessary is manipulated is not critical to the practice of my invention.

Thus, it will be appreciated by those of skill in the art that the unique compression means of the present invention provides many advantages. First, it permits one handed insertion and removal of the pessary, This frees up the person's second hand to increase the degrees of manipulation and thereby increase comfort in insertion, fit and removal. In addition, the unique compression means provides a way for the patient to remove and insert the pessary. This is especially useful for sexually active women.

The chamber 20 and plunger 30 may be made of any of a number of inert rigid resilient materials, such as plastic or rubber. The chamber 20 is preferably circular in cross-section to provide maximum comfort. The chamber 20 is tube-like and defines a hollow into which the plunger 30 is inserted. Since the plunger 30 is pressed into the chamber 20 and protrudes from the chamber 20 for attachment to the head 10, the plunger 30 should have longitudinal dimension larger than that of the chamber 20.

The plunger 30 consists of preferably two sections, an upper section 33 and lower section 32. The lower section 32 has a circular cross-section having diameter slightly smaller than the inner diameter of the chamber 20. The upper section 33 of the plunger 30 has yet a smaller diameter. A lower stop surface 35 defines the interface of the upper section 33 and lower section 32. The chamber 20 includes upper stop surface 22. Thus, when the plunger 30 is pressed into the chamber 20, the upper plunger section 33 moves past the upper stop surface 22 only as far as the lower stop surface 35 of the plunger 30.

The chamber 20 preferably also includes a spring 24. The spring 24 is positioned between the upper stop surface 22 and lower stop surface 35. Thus, it can be seen that the spring 24 provides increased pressure inside the chamber 20 to return the head 10 to the resting position. It is anticipated that, over time, the material of the head may lose its memory (elasticity). To compensate for this loss of memory, the spring 24 is preferably additionally provided.

Pessaries embodying the invention are preferably made in a range of head sizes. This permits the health professional to fit the pessary to the patient. Since the head is flexible and compressible, the size of the head 10 can be adjusted (within a limited range) to account for individual differences. Techniques for placement of pessaries are well known to those of skill in the art. Thus, maximum support and comfort are further achieved.

Figure 5:
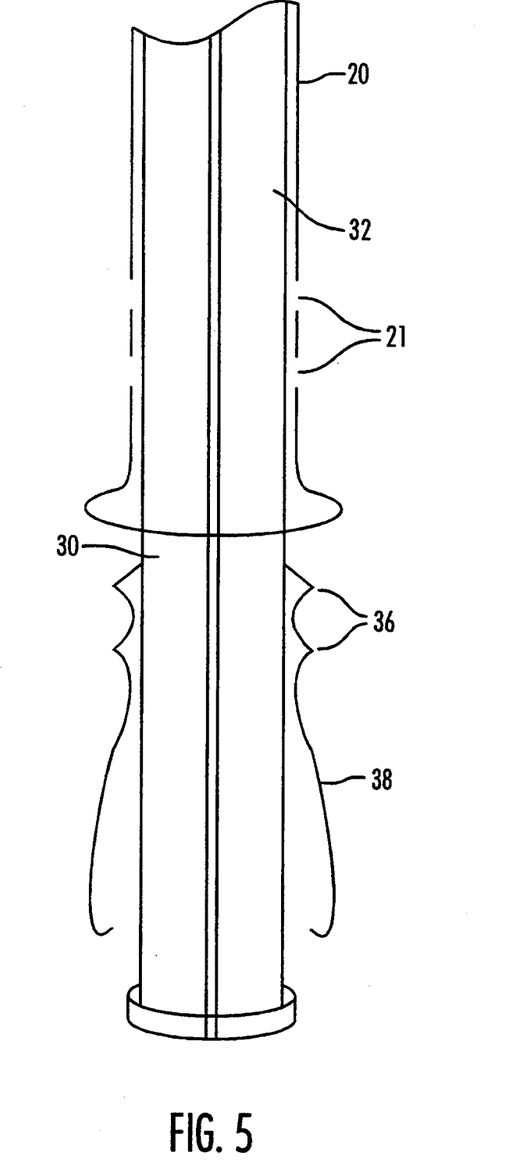
FIG. 5 shows a partial view of the chamber and plunger of a pessary including a locking mechanism according to the present invention.
Figure 6:
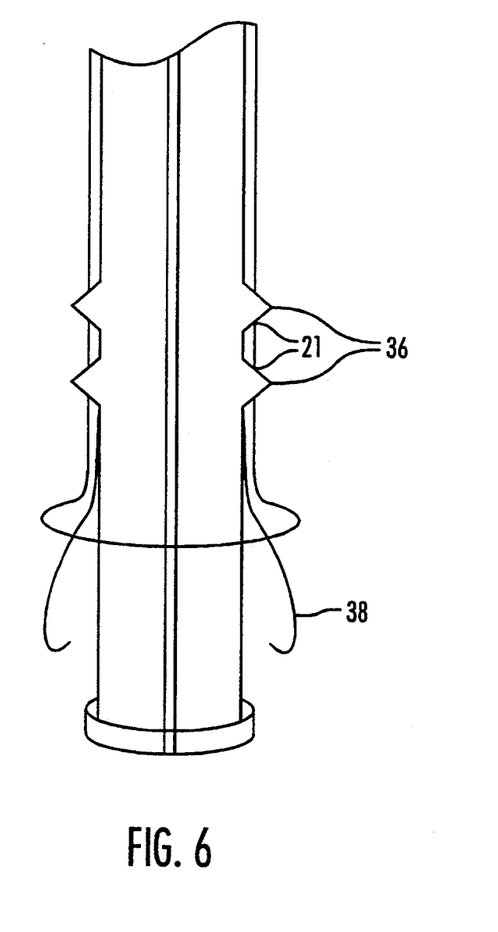
FIG. 6 shows a partial view as in FIG. 5 including an engaged locking mechanism.

Referring now to FIG. 5 there can be seen a partial sectional view of a manipulation apparatus for a pessary which includes a lock for holding the plunger 30 in the chamber 20. In this embodiment, the lock comprises lock adjuster arms 38 and lock engaging points 21. The lock adjuster arms 38 are attached to the plunger 30 in the lower section 32. As shown in FIG. 6, when the plunger 30 is pressed into the chamber 20, pressure points 36 of the lock adjuster arms 38 press inside of the chamber 20 until they press into the engaging points 21 of the chamber 20.

The primary utility provided by the lock is, upon insertion of the pessary, to retain a selected head size which is less than the fully extended position. Provision of the lock also permits easier installation and removal of a pessary of the preferred embodiment. In addition, by breaking down the insertion and removal procedures into a multiple step process, the need for greater strength and coordination is reduced. Since many users of pessaries are elderly, easier installation and removal is a great benefit.

The lock may have other embodiments from those shown. For example, the plunger 30 may have a row of bumps and the chamber 20 a corresponding row of holes or detents, so that the pessary may be locked in a variety of compressed or extended positions.

Figure 7:
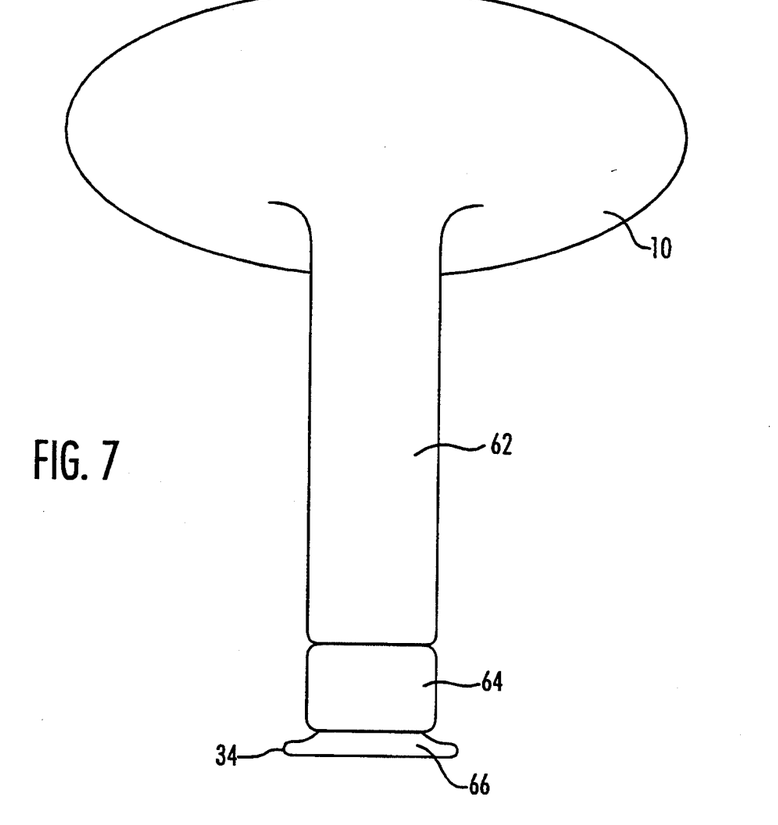
FIG. 7 shows a side view of a pessary of the present invention including an alternative locking mechanism.

An embodiment of the present invention having a different manipulation apparatus is shown in FIG. 7. The pessary shown in FIG. 7 includes a head 10, a chamber 62, a plunger 66, and a collar 64. In this embodiment, the chamber 62 and plunger 66 are attached to the head 10 as variously described. In this embodiment, however, the locking mechanism and means for compression are combined. The plunger 66 is preferably threaded. The collar 64 defines a hollow through which the plunger 66 may pass and includes threads complimentary to the threads on the plunger 66. Thus, by rotating the collar 64 about its longitudinal axis, the plunger 66 will move into or out of the chamber 62. It will thus be seen that this embodiment includes an automatic locking means, since the head 10 will remain in a set position unless the collar 64 is turned. As shown, the end of the plunger 66 includes an end 34 which prevents the plunger 66 from moving too far into the collar 64. The surface of the collar 64 preferably is textured so as to provide a positive grip to the person inserting or removing the pessary.

As a further alternative, the interior of the chamber 62 is threaded and the collar 64 is not used. Compression and extension of the head 10 is performed by turning the plunger 66 inside the chamber 62.

Figure 3:
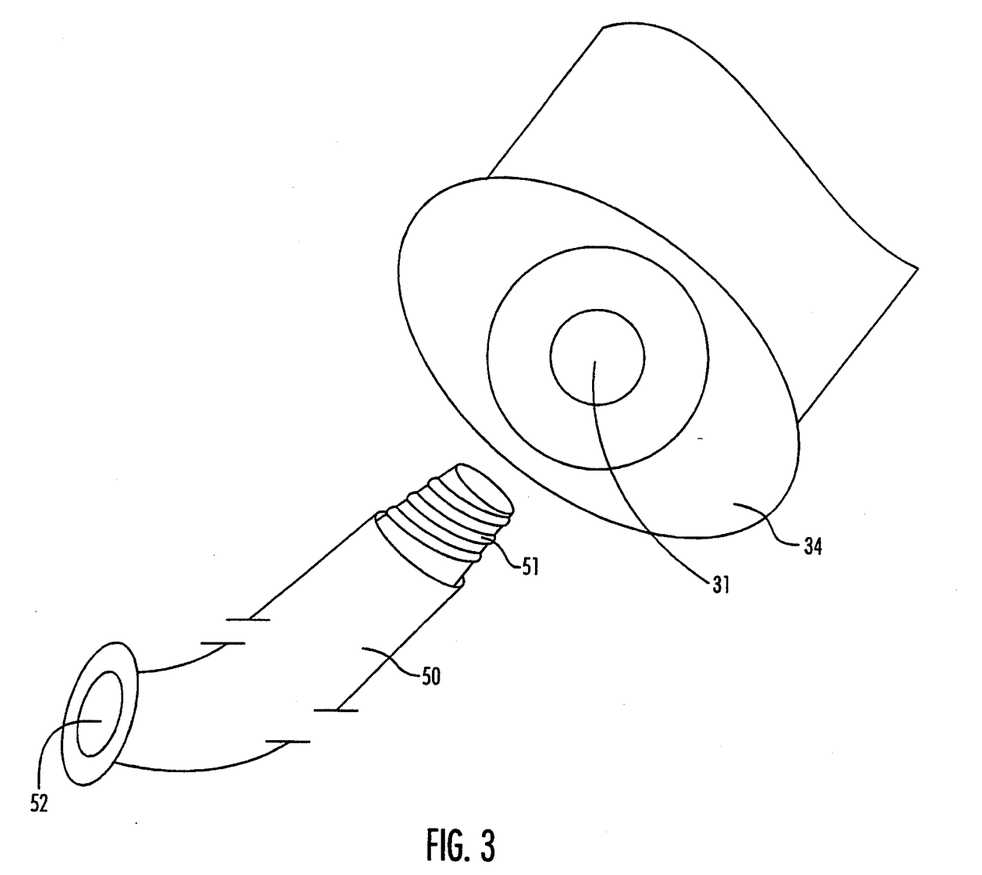
FIG. 3 shows a partial elevation of the pessary shown in FIG. 1 which includes a cleansing channel and optional flushing tube attachment.

Referring once again to FIG. 1, the plunger 30 preferably also defines a channel 31 along its longitudinal axis. The channel 31 passes through the head 10. By injecting a solution through the channel 31 the pessary, and the region of the vagina behind the pessary, may be cleansed. This clears the vaginal mucus and bacterial build-up which can create infection, foul odor and significant secretions. The channel may also include a plurality of tributaries from the channel 31 situated in the head 10 so that the solution sprays from various points of the head 10. Thus, the pessary and vagina may be thoroughly cleansed without requiring removal of the pessary. As shown in FIG. 3 a connection tubing 50 may be connected to the channel 31 so as to allow even greater flexibility in cleansing. The connecting end of the connection tubing 51 may be threaded or wedge shaped so as to fit inside of the channel 31. Both the channel outlet of the plunger 30 and the outlet 52 of the connection tubing 50 may be configured so as to allow attachment of a syringe or other device as is known in the art.

The present invention takes into consideration the need to allow fluid, such as cleansing fluids and mucus to drain from behind the pessary. Thus, the channel acts in two-way directions, providing both introduction and drainage.

Figure 4:
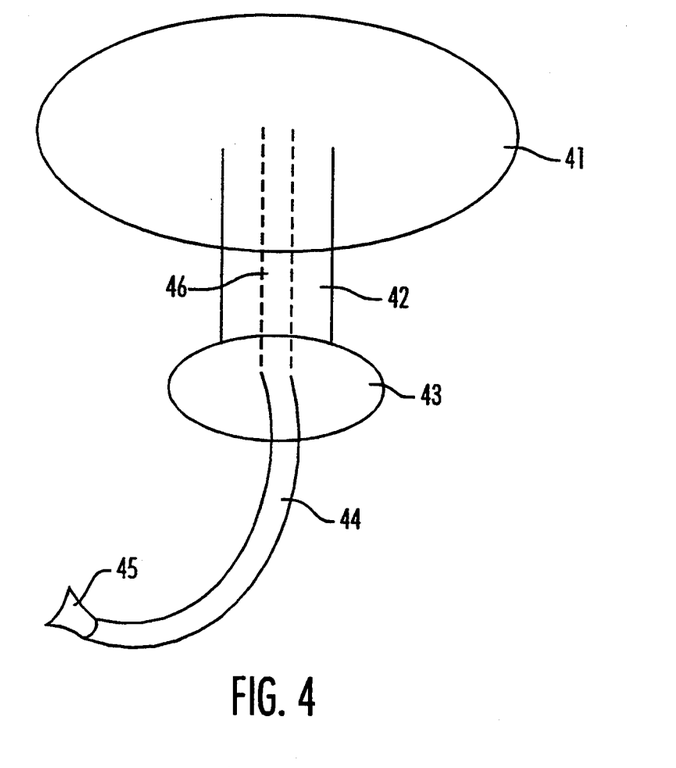
FIG. 4 shows a pessary embodying aspects of the invention particular to irrigation.

Referring now to FIG. 4, there is shown further aspects of the present invention relating to irrigation. This embodiment includes a head 41, a barrel 42 and a barrel grip 43. The barrel 42 defines a channel 46. The channel 46 continues past the barrel grip 43 and becomes a tube 44 having a connector 45. In this embodiment, the pessary is similar to the Gelhorn pessary known to those skilled in the art. However, this embodiment includes the novel irrigation means of the present invention. The tube 44 is preferably long enough so that when the pessary is inserted into the vagina, the tube extends to the opening of the vagina. This embodiment provides a very simplified pessary having the novel irrigation means of the present invention. Thus the pessary and the vagina may be cleansed without removal of the pessary by simply injecting a cleansing solution from, for example, a syringe, into the tube connector 45.

Although the present invention has been described in terms of a preferred embodiment above, numerous modifications and/or additions to the above-described preferred embodiment would be readily apparent to one skilled in the art. It is intended that the scope of the present invention extends to all such modifications and/or additions and that the scope of the present invention is limited solely by the claims set forth below,

I claim:

1. A pessary comprising:
a substantially flat, circular, flexible head substantially rigid across its diameter, the head partially compressible from small compressive forces, highly compressible from large compressive forces, and having an extended shape absent compressive forces, the head comprising a rim disposed about its circumference and two flat disks joined at the rim; and a manipulation apparatus operatively coupled to the head, the manipulation apparatus comprising a tube-like chamber and a plunger movably disposed inside the chamber, the plunger having a longitudinal dimension larger than that of the chamber;

wherein one disk extends between the rim and the plunger, and the other disk extends between the rim and the chamber, and operation of the manipulation apparatus provides large compressive forces on the head or release of previously set large compression forces.

2. The pessary of claim 1 wherein the head has an upper side and a lower side, the pessary further comprising means for allowing fluids to pass from one side of the head to the other.

3. The pessary of claim 1 wherein the plunger defines a channel along its longitudinal axis and extending past the head.

4. The pessary of claim 1 further comprising means for locking the head at a desired compressed position.

5. The pessary of claim 1 wherein the chamber further comprises at least one lock adjuster arm and the plunger further comprises at least one lock engager, wherein the lock adjuster arm secures the plunger to the chamber when placed in contact with the lock engager.

6. A pessary comprising:
a chamber defining a hollow;
a plunger disposed in the hollow and movable longitudinally therein; and
a head comprising a rim and a first and second plurality of disks, the disks connected to the rim and defining a hollow therebetween, the first disk connected to the chamber and operatively coupling the head to the chamber, and the second disk connected to the plunger and operatively coupling the head to the plunger,
so that movement of the plunger in the hollow changes the size of the head.

7. The pessary of claim 6 further comprising means for allowing fluids to pass beyond the head.

8. The pessary of claim 7 wherein the plunger defines a channel along its longitudinal axis and connected to the allowing means.

9. The pessary of claim 6 further comprising means for locking the plunger at a desired position on the chamber.

10. The pessary of claim 9 wherein the means for locking comprises at least one lock adjusting arm situated on the plunger and at least one lock engager on the chamber, wherein the lock adjusting arm secures the plunger to the chamber when placed in contact with the lock engager.

* * * * *